United States Patent [19]

Hoch et al.

[11] 4,111,903
[45] Sep. 5, 1978

[54] ORGANOTIN COMPOUNDS AND VINYL HALIDE RESIN COMPOSITIONS STABILIZED THEREWITH

[75] Inventors: Samuel Hoch, Brooklyn, N.Y.; Emery Szabo, Freehold, N.J.

[73] Assignee: Tenneco Chemicals, Inc., Saddle Brook, N.J.

[21] Appl. No.: 682,430

[22] Filed: May 3, 1976

[51] Int. Cl.² .................................................. C08J 3/20
[52] U.S. Cl. ............................ 260/45.75 S; 260/429.7
[58] Field of Search ........................ 260/429.7, 45.75 S

[56] References Cited

U.S. PATENT DOCUMENTS

| | | | |
|---|---|---|---|
| 2,731,484 | 1/1956 | Best | 260/429.7 |
| 2,752,325 | 6/1956 | Leistner et al. | 260/45.75 |
| 2,872,468 | 2/1959 | Leistner et al. | 260/429.7 |
| 3,115,509 | 12/1963 | Mack | 260/429.7 |
| 3,979,359 | 9/1976 | Kugcle et al. | 260/429.7 X |

FOREIGN PATENT DOCUMENTS 35-18387   1960   Japan.

*Primary Examiner*—Helen M. S. Sneed
*Attorney, Agent, or Firm*—Evelyn Berlow

[57] ABSTRACT

Sulfur-containing organotin compounds that are mobile liquids of low viscosity and that have a relatively mild sulfur odor have the structural formula

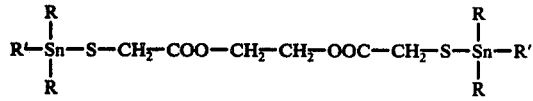

wherein each R represents an alkyl group having 1 to 8 carbon atoms, each R' represents $-S-(CH_2)_n-COOR''$, $-SR''$, or $-OOC-CH=CH-COOR'''$, R" represents an alkyl group having 8 to 18 carbon atoms, R'" represents an alkyl group having 3 to 18 carbon atoms, and $n$ is 1 or 2. These compounds can be used alone or in combination with other organotin compounds as stabilizers for vinyl halide resin compositions.

6 Claims, No Drawings

ORGANOTIN COMPOUNDS AND VINYL HALIDE RESIN COMPOSITIONS STABILIZED THEREWITH

This invention relates to novel sulfur-containing organotin compounds and to the use of these compounds as stabilizers for vinyl halide resin compositions. It also relates to vinyl halide resin compositions stabilized with these organotin compounds.

Organotin compounds that contain sulfur have long been recognized as highly effective stabilizers for vinyl halide resin compositions. The stabilizing effectiveness of these compounds is generally directly related to their tin content and to a lesser extent to their sulfur content. The organotin compounds that have high tin and sulfur contents, however, have several disadvantages that have severely limited their use. These compounds, which are expensive relative to other available stabilizers, often impart a yellow cast and haze to vinyl halide resin compositions during the first few minutes of heating, and they cause the development of a strong, unpleasant odor during processing. The unpleasant odor, color and haze frequently remain noticeable in the finished product. In addition, the organotin compounds that have high tin and sulfur contents are usually jelly-like or glassy, very viscous materials that are difficult to handle and to incorporate into resinous compositions.

In U.S. Pat. No. 2,752,325, Leistner et al. disclosed organotin compounds that were prepared by the reaction of an organotin oxide or organotin halide with an ester formed from one mole of a glycol and two moles of a mercapto-substituted carboxylic acid having 2 to 4 carbon atoms. Illustrative of the compounds disclosed in this patent is the compound having the structural formula

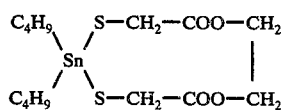

and its dimer, which has the structural formula

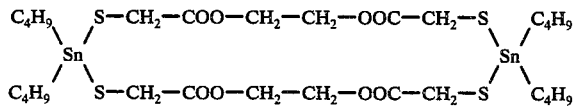

While these compounds are excellent stabilizers for vinyl halide resins, they are viscous, jelly-like, brown solids, and they have an exceptionally strong and unpleasant odor which remains noticeable in finished products that contain them.

In U.S. Pat. No. 3,819,673 and No. 3,936,482, Sagi et al. disclosed organotin compounds that are useful as catalysts in the polycondensation of organosilicon compounds. These compounds have the structural formula

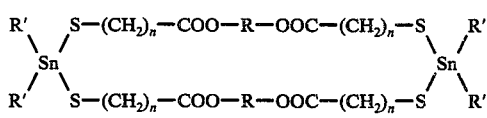

wherein each R represents a divalent hydrocarbon radical or a divalent radical consisting of divalent hydrocarbon radicals bonded to one another by —O—, —CO—, —COO—, or —CHOH— radicals; each R' represents a monovalent hydrocarbon radical, and n represents a positive number. The catalyst may also contain compounds of the structural formulas

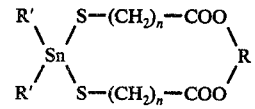

and

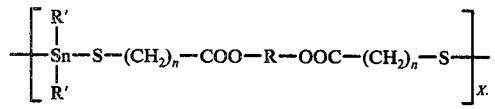

Like those disclosed by Leistner et al., these organotin compounds are dark, glassy, viscous materials that have a strong, unpleasant odor.

This invention relates to sulfur-containing organotin compounds that are mobile, low viscosity liquids that have a light color and a relatively mild odor. These compounds, which have a tin content of at least 20 percent, are very effective stabilizers for vinyl halide resins. Resinous compositions that contain them are characterized by excellent early color and clarity and long term heat stability as well as excellent processability and little or no odor. The structure of these compounds makes it possible to introduce long alkyl chains into them that improve their lubricating properties, as is required of stabilizers that are used in high friction processes.

The organotin compounds of this invention have the structural formula

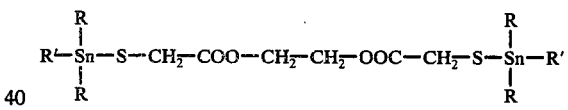

wherein each R represents an alkyl group having 1 to 8 carbon atoms, each R' represents —S—(CH$_2$)$_n$—COOR'', —SR'', or —OOC—CH=CH—COOR''', R'' represents an alkyl group having 8 to 18 carbon atoms, R''' represents an alkyl group having 3 to 18 carbon atoms, and n is 1 or 2.

Illustrative of the compounds of this invention are the following: bis(dimethyltin dodecyl thioglycolate) ethylene glycol dimercaptoacetate, bis(di-2-ethylhexyltin decyl thioglycolate) ethylene glycol dimercaptoacetate, bis(dioctyltin octadecyl mercaptopropionate) ethylene glycol dimercaptoacetate, bis(dibutyltin isooctyl mercaptopropionate)ethylene glycol dimercaptoacetate, bis(dimethyltin isooctyl mercaptide)ethylene glycol dimercaptoacetate, bis(dibutyltin decyl mercaptide)ethylene glycol dimercaptoacetate, bis(dioctyltin octadecyl mercaptide)ethylene glycol dimercaptoacetate, bis(dimethyltin propyl maleate)ethylene glycol dimercaptoacetate, bis(dibutyltin hexyl maleate)ethylene glycol dimercaptoacetate, bis(dioctyltin octadecyl maleate)ethylene glycol dimercaptoacetate, (dibutyltin dodecyl thioglycolate) (dibutyltin decyl mercaptide)ethylene glycol dimercaptoacetate, (dioctyltin isooctyl thioglycolate) (dioctyltin isooctyl maleate)ethylene glycol dimercaptoacetate, and (dibutyltin hexyl maleate) (dibutyltin dodecyl mercaptide)ethylene glycol dimercaptoacetate.

The compounds of this invention may be prepared by any suitable and convenient procedure. For example, they can be prepared by reacting one mole of ethylene glycol dimercaptoacetate with two moles of an organotin oxide or an organotin halide and two moles of an alkyl ester of a mercaptocarboxylic acid, an alkyl mercaptan, and/or a monoalkyl maleate. The reaction is usually carried out by heating the reactants at 70° to 100° C., preferably 90° to 95° C., under subatmospheric pressure until the theoretical amount of water has been evolved. The reaction mixture may be sparged with an inert gas, such as nitrogen, during the heating to assist in the removal of water from it. The products prepared in this way can be used without purification or further treatment to stabilize vinyl halide resin compositions.

The stabilizers of this invention may contain in addition to the novel organotin compounds other heat and light stabilizers, such as other organotin compounds, salts of barium, cadmium, strontium, zinc, and other polyvalent metals, organic phosphites, and polyhydric alcohols, lubricants, antioxidants, solvents, and the like.

In a preferred embodiment of the invention, stoichiometric excesses of an organotin oxide or organotin halide and of either ethylene glycol dimercaptoacetate or an alkyl mercaptocarboxylate, alkyl mercaptan, and/or monoalkyl maleate are used, and the product is a mixture of one of the compounds of this invention with another organotin compound.

Mixtures that have been found to be particularly valuable as stabilizers for vinyl halide resin compositions contain from 30 to 90 percent by weight of a compound having the structural formula

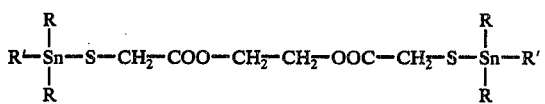

and from 10 to 70 percent by weight of a compound selected from the group consisting of compounds having the structural formula

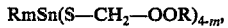

compounds having the structural formula

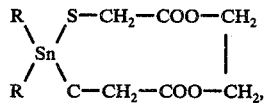

and mixtures thereof, wherein R, R', m, and n have the aforementioned significance. These mixtures, which are less expensive than the compounds of this invention, are light-colored non-viscous liquids that can be used to form stabilized vinyl halide resin compositions that have excellent early color and clarity and long term heat stability and that do not have a strong unpleasant odor.

Only a small amount of the organotin compounds of this invention or mixtures containing these compounds need be incorporated into the vinyl halide resin compositions to impart heat stability to them. As little as 0.2 percent of one of these compounds, alone or in admixture with another organotin compound, based on the weight of the vinyl halide resin, will bring about an appreciable improvement in the heat stability of the compositions. Five percent or more of the novel compounds can be used, but these larger amounts generally do not provide further improvement in the properties of the resinous compositions and for this reason are not ordinarily used. In most cases, from 0.5 percent to 3 percent by weight, based on the weight of the vinyl halide resin, of the organotin stabilizers of this invention gives most advantageous results.

The organotin stabilizers of this invention have been found to be excellent stabilizers for rigid vinyl halide resin compositions, that is, compositions that are formulated to withstand temperatures of at least 175° C. They are of particular value in the stabilization of rigid polyvinyl chloride compositions that are to be used in such high temperature fabrication processes as the blow molding of bottles. The novel stabilizers can also be used in plasticized vinyl halide resin compositions of conventional formulation where high softening point is not a requisite.

The vinyl halide resins that may be present in the stabilized compositions of this invention include both vinyl halide homopolymers, such as polyvinyl chloride, polyvinyl bromide, and polyvinylidene chloride, and copolymers formed by the polymerization of a vinyl halide with up to about 30 percent of a comonomer, such as vinyl acetate, vinyl propionate, vinyl butyrate, vinylidene chloride, ethylene, propylene, styrene, ethyl acrylate, methyl methacrylate, and the like. The invention is also applicable to mixtures of a vinyl halide resin in a major proportion with a minor proportion of another synthetic resin, such as chlorinated polyethylene, polyacrylate and polymethacrylate esters, polyacrylonitrile, and terpolymers of acrylonitrile, butadiene, and styrene. Any of the well known plasticizers for vinyl halide resins, such as dioctyl phthalate, dibutyl sebacate, tricresyl phosphate, and octyl diphenyl phosphate, can be present in the stabilized compositions.

In addition to the aforementioned ingredients, the stabilized resinous compositions may contain other resin additives, such as pigments, dyes, processing aids, impact modifiers, extenders, and lubricants, in the amounts ordinarily employed for the purposes indicated.

The stabilized vinyl halide resin compositions may be prepared by any suitable and convenient procedure. Such procedures include dry blending with a conventional mixer such as the Henschel blender, mixing on a two or three roll heated mill, and tumbling.

The invention is further illustrated by the following examples. In these examples, all parts are parts by weight and all percentages are percentages by weight.

EXAMPLE 1

A mixture of 384 grams (1.86 moles) of isooctyl thioglycolate, 195.6 grams (0.892 mole) of ethylene glycol dimercaptoacetate (95.8% assay), and 452 grams (1.79 moles) of dibutyltin oxide (47.1% Sn) was heated at 90°–95° C. at an absolute pressure of 100-110 mm. Hg and sparged with nitrogen until the theoretical 32 ml. of evolved water had been collected. After filtration, there was obtained 977.2 grams of bis(dibutyltin isooctyl thioglycolate) ethylene glycol dimercaptoacetate, a light yellow, mobile liquid that contained 21.2% Sn and 11.8% S (calculated: 21.1% Sn and 11.6% S).

EXAMPLE 2

A mixture of 192 grams (0.928 mole) of dodecyl mercaptan (97.8% assay), 97.8 grams (0.446 mole) of ethylene glycol dimercaptoacetate (95.8% assay) and 226 grams (0.896 mole) of dibutyltin oxide (47.1% Sn) was heated at 90°–100° C. at an absolute pressure of 90–100 mm. Hg and sparged with nitrogen until the theoretical 16 ml. of evolved water had been collected. After filtration, there was obtained 489.6 grams of bis(dibutyltin dodecyl mercaptide)ethylene glycol dimercaptoacetate, a light yellow, mobile liquid that contained 21.3% Sn and 11.6% S (calculated: 21.1% Sn and 11.6% S).

EXAMPLE 3

A mixture of 113.2 grams (0.869 mole) of isooctyl alcohol and 85.1 grams (0.869 mole) of maleic anhydride was heated at 100°–110° C. for 45 minutes and then cooled to 70° C. To the reaction mixture were added 97.8 grams (0.446 mole) of ethylene glycol dimercaptoacetate (95.8% assay) and 219.6 grams (0.869 mole) of dibutyltin oxide (47.1% Sn). The resulting mixture was heated at 95°–100° C. at an absolute pressure of 100–110 mm. Hg and sparged with nitrogen until 15.0 ml (theoretical 15.7 ml) of evolved water had been collected. After filtration, there was obtained 484.2 grams of bis(dibutyltin isooctyl maleate)ethylene glycol dimercaptoacetate, a yellow-orange liquid that contained 20.5% Sn and 5.7% S (calculated: 20.6% Sn and 5.7% S).

EXAMPLE 4

To a mixture of 600 grams of water and 544.8 grams (1.794 mole) of dibutyltin dichloride (39.1% Sn), which had been heated to 50°–55° C., was added 384 grams (1.86 moles) of isooctyl thioglycolate and 195.6 grams (0.892 mole) of ethylene glycol dimercaptoacetate (95.8% assay). The reaction mixture was stirred for 15 minutes after which 537.4 grams (3.44 moles) of a 25.6% sodium hydroxide solution was added to it over a period of 45 minutes while it was maintained at 50°–53° C. The reaction mixture was stirred for 45 minutes at 50°–55° C. and then allowed to separate into immiscible phases. The lower product layer was separated, heated at 90°–95° C. at an absolute pressure of 100 mm. Hg, and sparged with nitrogen to remove the evolved water. After filtration, there was obtained 979.5 grams of bis(dibutyltin isooctyl thioglycolate)ethylene glycol dimercaptoacetate, a light yellow, mobile liquid that contained 21.2% Sn and 11.6% S (calculated: 21.1% Sn and 11.6% S).

EXAMPLE 5

A mixture of 275 grams (1.33 moles) of isooctyl thioglycolate, 34.9 grams (0.159 mole) of ethylene glycol dimercaptoacetate (95.8% assay), and 205.4 grams (0.818 mole) of dibutyltin oxide (47.3Sn) was heated at 90°–95° C. at the absolute pressure of 100–110 mm. Hg and sparged with nitrogen until 14.0 ml. of water (theoretical, 14.7 ml.) of water) had been collected. After filtration, there was obtained 488.6 grams of a 35/65 blend of bis(dibutyltin isooctyl thioglycolate)ethylene glycol dimercaptoacetate and dibutyltin bis(isooctyl thioglycolate). The product was a light yellow liquid that was low in viscosity and that contained 19.3% Sn and 10.6% S (calculated: 19.2% Sn and 10.5% S).

EXAMPLE 6

A mixture of 320 grams (1.55 moles) of isooctyl thioglycolate, 244.6 grams (1.115 moles) of ethylene glycol dimercaptoacetate, and 468.6 grams (1.86 moles) of dibutyltin oxide (47.1% Sn) was heated at 90°–95° C. at the absolute pressure of 100 mm. Hg. and sparged with nitrogen until the theoretical 32.2 ml. of evolved water had been collected. After filtration, there was obtained 987 grams of an 86/14 blend of bis(dibutyltin isooctyl thioglycolate)ethylene glycol dimercaptoacetate and dibutyltin ethylene glycol dimercaptoacetate. The product was a yellowish liquid that was low in viscosity and that contained 22.1% Sn and 12.2% S (calculated: 22.0% Sn and 12.1% S).

EXAMPLE 7

A mixture of 100 parts of polyvinyl chloride (Tenneco 225), 1.5 parts of calcium stearate, 1.5 parts of acrylic resin (Tenneco Supercryl 100), 1.0 part of titanium dioxide, and 0.8 part of oxidized polyethylene was blended in a Henschel mixer at 3000 rpm at 60°–85° C. until a uniform composition was obtained. Sixty parts of the composition and 1.05 parts of one of the stabilizers of this invention or a comparative stabilizer were worked in a Brabender Plasticorder using a bowl temperature of 178° C. and a rotor speed of 60 rpm. Samples were removed at 2 minute intervals and observed for color development. The results are summarized in Table I. In this table, a rating of 1-2 indicates white; 3-4, off-white; 5-6, slightly yellow; 7-8, yellow; 9, dark yellow; and 10, tan.

Table I

| Ex. No. | Stabilizer | Color after indicated number of minutes in Brabender Plasticorder at 178° C. | | | | | | |
|---|---|---|---|---|---|---|---|---|
| | | 2 | 4 | 6 | 8 | 10 | 12 | 14 |
| 1A | Product of Ex. 1 | 1 | 4 | 5 | 6 | 7 | 8 | 10 |
| 1B | Product of Ex. 2 | 1 | 3 | 5 | 5 | 6 | 7 | 9 |
| 1C | Product of Ex. 4 | 1 | 4 | 5 | 6 | 7 | 8 | 10 |
| 1D | Product of Ex. 5 | 1 | 4 | 5 | 6 | 7 | 8 | 10 |
| 1E | Product of Ex. 6 | 1 | 3 | 5 | 5 | 6 | 7 | 9 |
| Comparative Example | Dibutyltin bis (isooctyl thioglycolate) | 2 | 5 | 6 | 7 | 8 | 10 | 10 |

From the data in Table I, it will be seen that the compositions containing the stabilizers of this invention have better early color and better color hold than the composition that contained dibutyltin bis(isooctyl thioglycolate), which is the standard thiotin stabilizer for use in rigid polyvinyl chloride compositions.

EXAMPLE 8

A plastisol was prepared by mixing 100 parts of polyvinyl chloride (Tenneco 1755) with 60 parts of dioctyl phthalate, 5 parts of epoxidized 2-ethylhexyl tallate, and 1.65 parts of either bis(dibutyltin isooctylmaleate)ethylene glycol dimercaptoacetate or dibutyltin bis(n-propyl maleate).

A 0.020 inch film of each of the plastisols was drawn down on a glass plate and cured for 5 minutes at 195° C. The heat stability of the compositions was determined by placing chips that had been cut from the films in a forced-circulation oven at 195° C., and removing them periodically until degradation was complete as indicated by color change. The results obtained are summarized in Table II. In this table, a rating of 1-2 indicated clear and colorless; 3-4, a slightly yellow tint; 5-6, yellow; 7-8, dark yellow; 9, amber; and 10, dark amber.

Table II

| Heat Stability (Color after indicated number of minutes at 195° C.) | Stabilizer Bis(dibutyltin isooctyl maleate) ethylene glycol dimercaptoacetate | Dibutyltin bis(n-propyl maleate) |
| --- | --- | --- |
| 0 | 1 | 1 |
| 5 | 1 | 2 |
| 10 | 1 | 2 |
| 15 | 2 | 3 |
| 20 | 2 | 4 |
| 25 | 5 | 6 |
| 30 | 6 | 7 |
| 35 | 8 | 9 |
| 40 | 10 | 10 |

The data in Table II show that the plastisol composition containing the stabilizer of this invention is superior in both early color and long term color hold to that containing dibutyltin bis(n-propyl maleate), which is a standard organotin stabilizer for plastisol formulations.

What is claimed is:

1. A heat and light stable resinous composition comprising a vinyl halide resin and 0.2 percent to 5 percent by weight, based on the weight of the vinyl halide resin, of an organotin compound having the structural formula

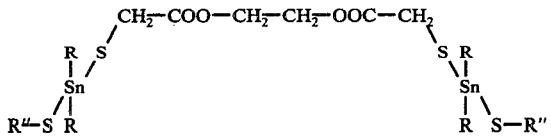

wherein each R represents an alkyl group having 1 to 8 carbon atoms and each R" represents an alkyl group having 8 to 18 carbon atoms.

2. A heat and light stable resinous composition as defined in claim 1 wherein the vinyl halide resin is polyvinyl chloride.

3. A heat and light stable resinous composition as defined in claim 1 that contains from 0.5 percent to 3 percent by weight, based on the weight of the vinyl halide resin, of the organotin compound.

4. A heat and light stable resinous composition as defined in claim 1 wherein the organotin compound is bis(dibutyltin dodecyl mercaptide) ethylene glycol dimercaptoacetate.

5. An organotin compound having the structural formula

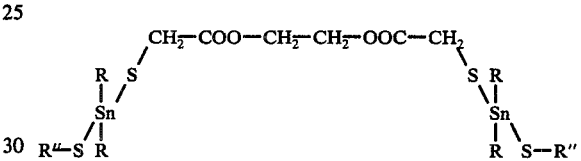

wherein each R represents an alkyl group having 1 to 8 carbon atoms and each R" represents an alkyl group having 8 to 18 carbon atoms.

6. The organotin compound defined in claim 5 that is bis(dibutyltin dodecyl mercaptide)ethylene glycol dimercaptoacetate.

* * * * *